US 6,696,618 B2

(12) United States Patent
Dodge, II et al.

(10) Patent No.: US 6,696,618 B2
(45) Date of Patent: Feb. 24, 2004

(54) ABSORBENT COMPOSITES EXHIBITING SWELLING/DESWELLING PROPERTIES (75) Inventors: Richard Norris Dodge, II, Appleton, WI (US); Xiaomin Zhang, Appleton, WI (US); Jian Qin, Appleton, WI (US); Fu-Jya Daniel Tsai, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 91 days.

(21) Appl. No.: 10/015,936

(22) Filed: Dec. 12, 2001

(65) Prior Publication Data
US 2003/0109840 A1 Jun. 12, 2003

(51) Int. Cl.$^7$ .................................. A61F 13/15
(52) U.S. Cl. ................. 604/367; 604/364; 604/365; 604/368
(58) Field of Search ........................ 604/364, 365, 604/366, 367, 368, 372, 375, 377, 376; 428/402, 402.2, 402.21–402.24, 403, 407, 913; 442/301, 414; 525/221, 222

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,548,847 A * | 10/1985 | Aberson et al. ............ 428/74 |
| 5,226,902 A | 7/1993 | Bae et al. |
| 5,393,602 A | 2/1995 | Urry |
| 5,520,672 A | 5/1996 | Urry |
| 5,562,646 A | 10/1996 | Goldman et al. |
| 5,599,335 A | 2/1997 | Goldman et al. |
| 5,641,562 A | 6/1997 | Larson et al. |
| 5,669,894 A | 9/1997 | Goldman et al. |
| 5,836,929 A | 11/1998 | Bewick-Sonntag et al. |
| 5,843,575 A | 12/1998 | Wang et al. |
| 5,849,405 A | 12/1998 | Wang et al. |
| 5,855,571 A * | 1/1999 | Steger et al. ............ 604/368 |

(List continued on next page.)

FOREIGN PATENT DOCUMENTS

| EP | 532 002 | 3/1993 |
| EP | 693 508 | 1/1996 |
| EP | 944 402 | 10/1997 |
| WO | 98/24832 | 6/1998 |
| WO | 99/03435 | 1/1999 |
| WO | 99/49908 | 10/1999 |
| WO | 01/34677 | 5/2001 |
| WO | 01/47568 | 7/2001 |
| WO | 01/47570 | 7/2001 |

Primary Examiner—Weilun Lo
Assistant Examiner—Jacqueline Stephens
(74) Attorney, Agent, or Firm—Pauley Petersen & Erickson (57) ABSTRACT This invention relates to an absorbent composite which utilizes multifunctional superabsorbent materials to enhance distribution of fluids within the absorbent composite. More specifically, this invention relates to superabsorbent materials which swell and absorb fluids and also can deswell and release fluids into the surrounding absorbent composite and towards additional superabsorbent material. The superabsorbent materials of this invention deswell and release fluid by means of a triggering mechanism. Triggering mechanisms can include thermal, chemical, mechanical, electronic, magnetic, and radiation energies. Swelling and deswelling of the superabsorbent materials can be repeated for more than one cycle thereby improving fluid distribution. Multiple swelling and deswelling cycles allow multiple insults to be distributed throughout an absorbent composite, fully utilizing the absorbent capabilities of the full absorbent composite and minimizing leakage.

87 Claims, 4 Drawing Sheets

U.S. PATENT DOCUMENTS

| | | |
|---|---|---|
| 5,855,572 A | 1/1999 | Schmidt |
| 5,858,535 A | 1/1999 | Wang et al. |
| 5,977,014 A | 11/1999 | Plischke et al. |
| 5,998,695 A | 12/1999 | Roe et al. |
| 6,011,196 A | 1/2000 | Wang et al. |
| 6,018,093 A | 1/2000 | Roe et al. |
| 6,099,950 A | 8/2000 | Wang et al. |
| 6,121,509 A | 9/2000 | Ashraf et al. |
| 6,152,904 A | 11/2000 | Matthews et al. |
| 6,160,198 A | 12/2000 | Roe et al. |
| 6,160,200 A | 12/2000 | Ehrnsperger et al. |
| 6,186,991 B1 | 2/2001 | Roe et al. |
| 6,232,520 B1 | 5/2001 | Hird et al. |
| 6,238,379 B1 | 5/2001 | Keuhn, Jr. et al. |
| 6,258,996 B1 | 7/2001 | Goldman |
| 6,398,769 B1 * | 6/2002 | Fernkvist et al. ...... 604/385.01 |

* cited by examiner

Cradle S/D Test (33g/insult, 3 insults)

ABSORBENT COMPOSITES EXHIBITING SWELLING/DESWELLING PROPERTIES

FIELD OF THE INVENTION

This invention relates to an absorbent composite having a fibrous matrix and at least one superabsorbent material. At least one of the superabsorbent materials is capable of swelling during fluid absorption and, by application of a triggering mechanism, deswelling to release and reswelling to absorb at least some of the absorbed fluid. In one embodiment of this invention this swelling, deswelling, and reswelling of the superabsorbent materials is repeatable.

BACKGROUND OF THE INVENTION

Superabsorbent materials are useful in personal care absorbent articles for absorbing a large amount of fluids. Superabsorbent materials are often combined with water-insoluble fibers to create an absorbent composite for use in an absorbent core of an absorbent article. Recent improvements in absorbent composites have increased fluid intake rates of the absorbent composites complementing the absorbent composite absorbent capacities. However, current absorbent composites useful in absorbent cores of absorbent articles generally have inadequate, or less than desirable, fluid distribution properties. Poor fluid distribution decreases the full utility efficiency of absorbent composites as not all the superabsorbent material is absorbing liquid.

Fluid distribution in an absorbent composite is generally dependent on the amount of free liquid available for distribution, the structure and materials of the absorbent composite, and a time factor. One potential solution known in the art for improving fluid distribution in an absorbent composite is to use superabsorbent materials having a slow absorbency rate. The theory for using slow absorbency superabsorbent materials is that there would be diminished or delayed gel blocking and thereby providing more free liquid and time for the liquid to distribute away from the insult target area. However, although distribution was enhanced using the slow superabsorbent, the absorbent composite typically did not provide necessary leakage protection. The extra free liquid not absorbed quickly by the slow absorbency superabsorbent would leak from the absorbent composite and eventually from the absorbent article.

As can be seen in the use of slow absorbency superabsorbent materials, there is a conflict between the functions of leakage and distribution. One problem with the use of slow swelling rate superabsorbent materials in an absorbent composite is that the time required to lockup liquid into the superabsorbent material is relatively long. It is this free liquid which is believed to be responsible for leakage of liquid from an absorbent product while in use. To reduce leakage, the absorbent composite needs to lockup liquid at a rate similar to the liquid delivery rate. However, if the superabsorbent materials absorb the liquid, then distribution of liquid is reduced since there is no free liquid to be distributed. The inventors have conceived of and demonstrated one way to rectify this conflict. Using superabsorbent materials that have the ability to quickly lockup liquid and then gradually release this liquid so that it can be distributed will result in desirable leakage and distribution behavior.

There is a need for an absorbent composite that has enhanced fluid distribution properties while maintaining enhanced lockup properties, thereby maximizing the absorbent capabilities of superabsorbent materials.

SUMMARY OF THE INVENTION

This invention relates to an absorbent composite which utilizes multifunctional superabsorbent materials to enhance distribution of fluids. Current commercial superabsorbents have one single function, to swell and absorb fluids. This invention relates to the use of superabsorbent materials which swell and absorb fluids, and which also can deswell and release fluids into the surrounding composite and towards additional superabsorbent material that is away from an intake area.

The superabsorbent materials of this invention swell during absorption of fluids and, in one embodiment, are triggered to deswell and release fluid by a triggering mechanism. The free liquid released by the triggered deswelling is then free to be distributed away from the target area where the initial insult occurred. Triggering mechanisms include, without limitation, thermal, chemical, mechanical, electronic, magnetic, and radiation energies. In one embodiment of this invention the swelling and deswelling of the superabsorbent materials can be repeated for more than one cycle. Multiple swelling and deswelling cycles allow multiple insults of liquid to be locked up, released, and then distributed throughout an absorbent composite, fully utilizing the absorbent capabilities of the full absorbent composite and minimizing leakage.

One embodiment of this invention relates to an absorbent composite having a combination of swelling/deswelling superabsorbents and superabsorbents that do not deswell. In one embodiment the superabsorbent materials capable of swelling or deswelling are placed in the target area, or the area where the fluid insult is initially applied, and away from the target area is additional superabsorbent materials capable of fast absorption. The swelling/deswelling superabsorbent materials quickly absorb the initial insult and are then triggered to deswell, thereby distributing the absorbed liquid to the superabsorbent material away from the target area. In one embodiment all the superabsorbent material is capable of swelling and deswelling but the trigger is activated only to superabsorbent materials in the target area receiving the first fluid thereby deswelling and distributing the released fluid to the surrounding superabsorbent material which was not triggered.

An additional embodiment of this invention relates to an absorbent composite in which a first superabsorbent material that swells slowly is located in a target area. A second superabsorbent material that is capable of swelling and deswelling is placed just outside the target area of the absorbent composite. A normal or fast swelling rate third superabsorbent material is located in the absorbent composite such that the swelling and deswelling superabsorbent is located between the slow swelling rate superabsorbent and the normal or fast swelling rate superabsorbent.

Further embodiments and advantages of this invention will be described below in the Detailed Description of the Presently Preferred Embodiments.

DEFINITIONS

Within the context of this specification, each term or phrase below will include the following meaning or meanings.

"Absorbent article" includes without limitation diapers, training pants, swim wear, absorbent underpants, baby wipes, adult incontinence products, feminine hygiene products, and protective garments including without limitation medical garments, underpads, bandages, absorbent drapes, and medical wipes, as well as industrial work wear garments.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid. The term also includes film-like materials that exist as open-celled foams.

"Foam" refers to two-phase gas-solid systems that have a supporting solid lattice of cell walls that are continuous throughout the structure. The gas, typically air, phase in a foam is usually distributed in void pockets often called cells. The cells typically have openings to permit fluid communication from one cell to another. In other words, the individual cells of the foam are not completely isolated from each other by the polymeric material of the cell walls. The cells in such substantially open-celled foam structures have intercellular openings which are large enough to permit fluid transfer from one cell to another within the foam structure.

"Free space of the absorbent composite" refers to the open areas, or porous area, within the fibrous matrix of the absorbent composite. Absorbent composites of this invention typically have a porous structure with open space within the fibrous matrix containing superabsorbent materials.

"Hydrophilic" describes fibers or the surfaces of fibers which are wettable by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Leg elastic" includes elastic bands, strands, ribbons, filaments, filament bunches and the like, which are adjacent to a garment opening that receives a wearer's leg.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent" or "superabsorbent material" refers to a water-swellable, water-insoluble organic or inorganic material capable, under the most favorable conditions, of absorbing at least about 10 times its weight and, more desirably, at least about 15 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

Figure 1:
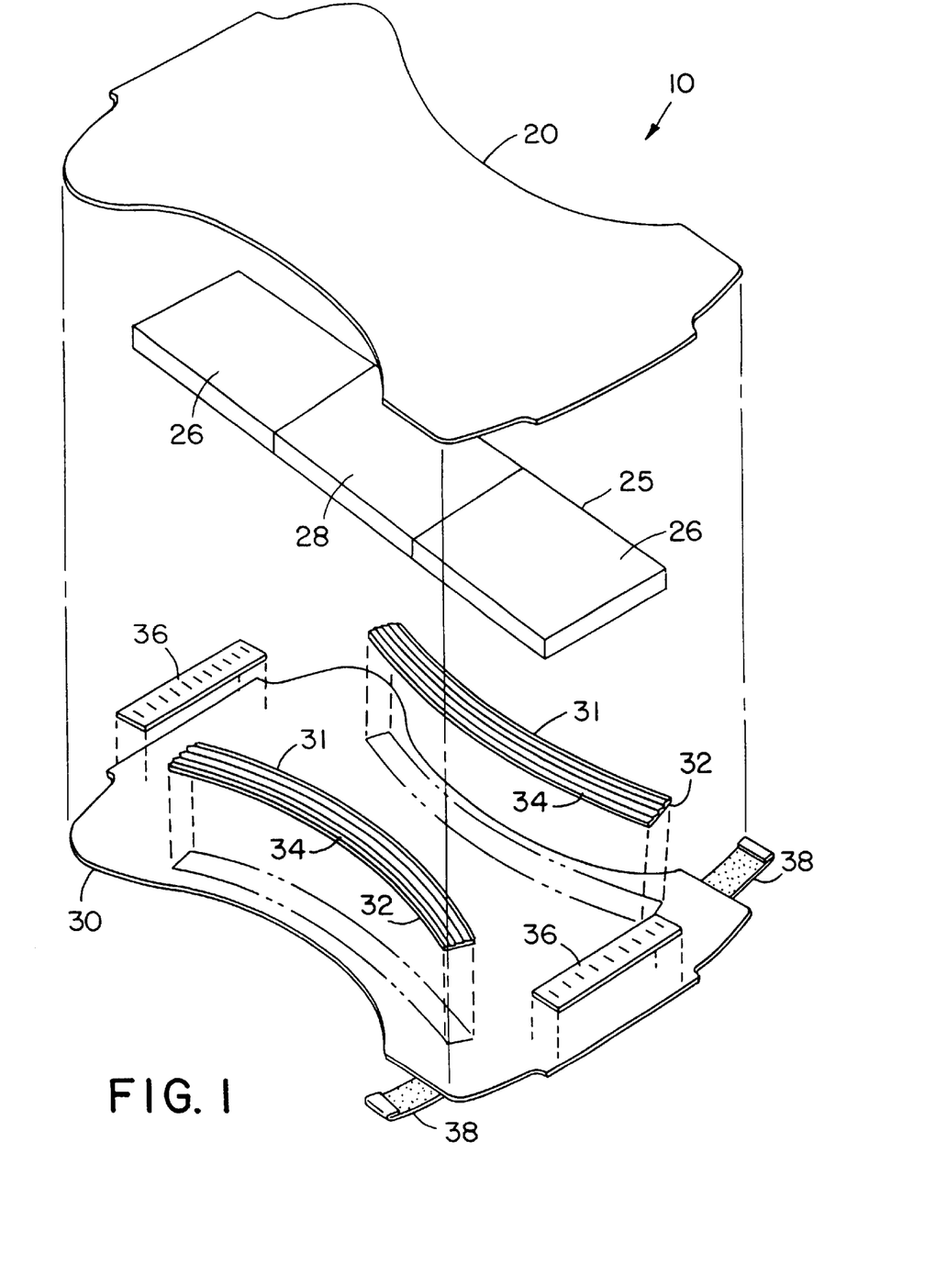
FIG. 1 is an exploded perspective view of an absorbent article according to one embodiment of this invention.

Absorbent composites of this invention are useful in personal care absorbent articles such as diapers, training pant, swim wear, feminine care products, and medical absorbent products. FIG. 1 illustrates an exploded perspective view of a typical disposable diaper according to one embodiment of this invention. Referring to FIG. 1, disposable diaper 10 includes outer cover 30, body-side liner 20, and absorbent core 25 between body-side liner 20 and outer cover 30. Outer cover 30 is constructed of conventional non-absorbent materials. By "non-absorbent" it is meant that these materials have an absorptive capacity not exceeding 5 grams of 0.9% by weight aqueous sodium chloride solution per gram of material. INDA Standard Test Method IST 10.1 (95), "Standard Test Method for Absorbency Time, Absorbency Capacity, and Wicking Time," published by INDA, Association of the Nonwoven Fabrics Industry, Cary, N.C., provides the basis for a suitable test method to measure absorbency, and is incorporated by reference.

Body-side liner 20 is constructed from highly liquid pervious materials. Body-side liner 20 functions to allow liquid from the wearer to contact the absorbent material or superabsorbent material present in diaper 10. Body-side liner 20 can be made from materials including porous woven materials, porous nonwoven materials, films with apertures, open-celled foams, and batting.

Additionally, a surge layer made from nonwoven fibers can be added between body-side liner 20 and absorbent core 25. Surge layers comprises surge material having an operable level of density and basis weight to quickly collect and temporarily hold liquid surges, to transport the liquid from its initial entrance point and to substantially release the liquid to absorbent core 25 and the superabsorbent material in absorbent core 25.

One embodiment of diaper 10 comprises a barrier tissue between body-side liner 20 and absorbent core 25. Alternatively, the barrier tissue may be between a surge layer and body-side liner 20 or between the surge layer and absorbent core 25. A barrier tissue is beneficial in keeping any loosened superabsorbent material from passing through body-side liner 20 and contacting the user. Barrier tissues are typically natural fiber materials such as any type of wood pulp. Barrier tissues can also be made from uncreped through air-dried (UCTAD) tissue material known in the art.

Outer cover material 30 maybe breathable to water vapor. Outer cover 30 desirably includes a material that is substantially liquid impermeable, and can be elastic, stretchable or nonstretchable. The outer cover 30 can be a single layer of liquid impermeable material, but desirably includes a multi-layered laminate structure in which at least one of the layers is liquid impermeable. For instance, the outer cover 30 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture and/or mating fastening component qualities. One example of such a material is a 20 gsm (grams per square meter) spunbond polypropylene nonwoven web. The outer layer may also be made of those materials of which liquid permeable bodyside liner 20 is made. While it is not a necessity for the outer layer to be liquid permeable, it is desired that it provides a relatively cloth-like texture to the wearer.

The inner layer of the outer cover 30 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 30 when a single layer, prevents waste material from wetting articles, such as bedsheets and clothing, as well as the wearer and care giver. A suitable liquid impermeable film for use as a liquid impermeable inner layer, or a single layer liquid impermeable outer cover 30, is a 0.2 millimeter polyethylene film commercially available from Huntsman Packaging of Newport News, Va., U.S.A. If the outer cover 30 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 30. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Generally outer cover 30 will have a moisture vapor transmission rate (MVTR) of at least about 300 grams/$m^2$-24 hours, preferably at least about 1000 grams/$m^2$-24 hours, more preferably at least about 3000 grams/$m^2$-24 hours, measured using INDA Test Method IST-70.4-99, herein incorporated by reference.

Attached to outer cover 30 are waist elastic members 36, fastening tapes 38, and leg elastic members 31. The leg elastics 31 comprise a carrier sheet 32, which can be a polyolefin film, and individual elastic strands 34. The waist elastic members 36 and the leg elastic members 31 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 31 include a plurality of dry-spun coalesced multifilament spandex elastomeric threads sold under the trade name LYCRA® and available from E.I. DuPont de Nemours and Company, Wilmington, Del., U.S.A.

The diaper of FIG. 1 is a general representation of one basic diaper embodiment. Various modifications can be made to the design and materials of diaper parts. The various layers of article 10 have dimensions which vary depending on the size, shape, and needs of the wearer.

Absorbent core 25 typically comprises absorbent materials including natural fibers such as wood pulp fibers. Absorbent core 25 can also include nonwoven fibers or webs. "Nonwoven" and "nonwoven web" refer to materials and webs of material which are formed without the aid of a textile weaving or knitting process. Absorbent core 25 typically comprises a matrix of hydrophilic fibers, such as a web of cellulosic fluff, mixed with particles of a superabsorbent material. In a particular embodiment, absorbent core 25 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. Examples of fiber materials used in absorbent core 25 include, without limitation, wood pulp fluff, cotton, wool, silk, polyethylene, polypropylene, polyester, nylon, polyvinyl alcohol, polyacrylonitrile, and polyvinyl chloride.

The superabsorbent material according to this invention can be in the form of fibers, particles, filaments, or printed or coated onto a fiber matrix. The superabsorbent material can be substantially homogeneously mixed with the hydrophilic composite fluff matrix or can be nonuniformly mixed. The fluff and superabsorbent particles can also be selectively placed into desired regions of the absorbent core 25 to better contain and absorb body exudates. The concentration of the superabsorbent particles can also vary through the thickness of the absorbent core 25. Alternatively, absorbent core 25 can include a laminate of fibrous webs and superabsorbent material or other suitable means of maintaining a superabsorbent material in a localized area.

In one embodiment of this invention the superabsorbent material is capable of swelling and absorbing fluid and, when a triggering mechanism is applied, deswelling and releasing fluids. "Swelling" refers to the growth in size of the superabsorbent material that occurs while fluids are being absorbed by the superabsorbent material. For swelling to occur in superabsorbent materials fluids must be absorbed, therefore to say a superabsorbent material is swelling also means the superabsorbent material is absorbing. "Deswelling" refers to the decrease in size of the superabsorbent material that occurs while fluids are being desorbed from the superabsorbent material. For deswelling to occur in superabsorbent material the absorbed fluids must be desorbed, or released from the superabsorbent material, therefore, to say a superabsorbent material is deswelling also means the superabsorbent material is releasing liquid.

A solution of 0.9% by weight sodium chloride, known in the art as a substitute for bodily fluids, is useful for quantifying the swelling and deswelling of superabsorbent materials. Superabsorbent materials according to this invention are capable of swelling, or absorbing, at least about 10 grams of 0.9% by weight sodium chloride solution per gram of superabsorbent (g/g), more suitably at least about 15 g/g, and desirably at least about 20 g/g.

Superabsorbent materials of this invention are capable of deswelling and desorbing fluids after a triggering mechanism is applied. In one embodiment of this invention, triggering mechanisms function after the superabsorbent materials is saturated, or substantially saturated, with absorbed liquid. The triggering mechanism causes the superabsorbent material to deswell and release the absorbed liquid. Trigger mechanisms useful in this invention include, without limitation, materials which react to thermal, chemical, mechanical, electrical, magnetic, or radiation energy. Triggering mechanisms may also include a combination of these mechanisms or other mechanisms which can cause superabsorbent materials to releases the absorbed fluids.

Triggering mechanisms can be applied to the absorbent composite by means of blending, encapsulation, coating, printing, laminating, strategically blending and/or placing in specific pocket of the composites, combinations of these, or other means. Triggering mechanism may have time delayed effects, and only start to function when such effects are eliminated. The triggering materials may be used synergistically with or without any time-controlled release or delay functions.

In one embodiment of this invention the absorbent composite has a temperature sensitive superabsorbent gel, such as a N-isopropylacrylamide-sodium acrylate polymer (NIPA), and a temperature change activates the triggering mechanism. Other polymers suitable for temperature sensitive superabsorbent polymers include, but are not limited to, cross linked template polymerized absorbent polymers, for example, polyethylene oxide-sodium polyacrylate polymer, polyethyleneoxide-polypropleneoxide-sodium polyacrylate polymer, or sodium-acrylate grafted copolymers, such as sodium acrylate grafted hydroxypropyl cellulose copolymer.

In one embodiment of this invention a change in temperature triggers the NIPA to release absorbed liquid into the free space of the absorbent composite. NIPA used in this invention has a phase transition temperature of about 39° C. NIPA will absorb liquid at a temperature lower than about 39° C., and when the temperature is raised to or above about 39° C. the NIPA shrinks and squeezes out the absorbed liquid to the free space of the absorbent composite where the liquid can be absorbed by other superabsorbent materials. If the temperature is then lowered below about 39° C. the NIPA is capable of reswelling and absorbing more fluids from the free space of the absorbent composite or a subsequent insult.

Without intending to be bound thereby, it is hypothesized that the temperature sensitive phenomenon in regards to the swelling is due to the intermolecular attraction change between certain special segments on the polymer chains and water molecules. These special segment (i.e., functional groups, repeating unit or chain segments) have strong intermolecular bonding energy with water at a low temperature, which causes water molecules to diffuse into the polymer networks (swelling). When the temperature rises over the phase transition temperature, the segments undergo a drastic change and completely lose the strong intermolecular bonding energy. The segments at such stage are no longer absorbing water and actually give up the absorbed water (deswelling). There are many macromolecular phase transitions exhibiting such drastic change. For example, a segment can change from exhibiting hydrophilic characteristics to hydrophobic characteristics because temperature rise causes conformation change of the segment from exposing hydrophilic functional groups to exposing hydrophobic backbone chain. For another example, some polymer may change solubility due to a rise in temperature so that its macromolecular chain networks may change from an extended conformation (swollen) to a collapsed conformation (deswollen).

In one embodiment of this invention the swelling-deswelling-reswelling cycle can be repeated multiple times. One advantage to using temperature changes to swell and deswell superabsorbent materials is that no additional triggering agent needs to be added.

In one embodiment of this invention conventional superabsorbent materials can be triggered to deswell by a change in pH of the superabsorbent environment. It has been discovered that current commercial superabsorbents can be triggered to deswell by the addition of an acidic compound or solution. In one embodiment of this invention, a hydrochloric acid solution is applied to the swollen superabsorbent material, which causes the superabsorbent material to deswell and release the fluid to the free space of the absorbent composite to be distributed to additional superabsorbent materials throughout the absorbent composite. A basic compound or solution is then used to trigger the deswelled superabsorbent material to reswell. In a real absorbent product application, a weakly acidic compound as well as a weakly basic compound is preferred. Also, the acid/base in the form of solid is preferred. Using weaker acids and bases such as citric acid and baking soda in the absorbent composite is safer for the user than stronger acids and bases such as hydrochloric acid and sodium hydroxide. In one embodiment of this invention the desirable pH range for an absorbent composite comprising the acid/base triggering superabsorbent material to swell and deswell is about 4 to 7. To deswell the superabsorbent material the pH is lowered to the lowest pH value of polyacrylic acid (about 4) when a weak acid, such as citric acid is used to trigger deswell. To reswell the superabsorbent the pH is returned to the original pH value of the superabsorbent material at 70% neutralization, which is at about 6.5 when a weak base, such as $NaHCO_3$, is used. When an acid or a base is used as a deswelling/swelling trigger, it cannot be directly blended with a superabsorbent material because a trigger has to function at an appropriate time. In order to activate the triggers with a delayed effect at various lengths of time, the acid and/or base has to be shielded from direct or immediate contact with bodily fluid. Encapsulation of the acid and/or base with certain chemical coatings with different thickness and dissolution kinetics can achieve the time-delayed effect.

In one embodiment of this invention the absorbent composite has a water-insoluble fibrous matrix, a superabsorbent material, and an encapsulated triggering mechanism. The first encapsulated triggering mechanism has a suitable first release time of about 5 to 60 minutes. The release time is the time required to dissolve or substantially dissolve the encapsulation material encapsulating the triggering mechanism, thereby allowing the triggering mechanism to effect the superabsorbent material. The initial absorbency of the superabsorbent material before the first triggering mechanism is released is suitably at least about 10 grams fluid per gram of superabsorbent material, more suitably at least 15 grams fluid per gram of superabsorbent material, and desirably at least about 20 grams fluid per gram of superabsorbent material. After the triggering mechanism has been released the superabsorbent material has a second absorbency of at least about 20% less than the initial absorbency, more suitably at least about 25% less than the initial absorbency, and desirably at least about 30% less than the initial absorbency.

The first encapsulated triggering mechanism can comprise any triggering mechanism of this invention depending on the type of superabsorbent material. In one embodiment the first triggering mechanism includes either an acid or a base. If the superabsorbent material is an anionic superabsorbent material then the first triggering mechanism will include an acid. If the superabsorbent material is a cationic superabsorbent material then the first triggering mechanism includes a base.

In one embodiment of this invention the absorbent composite contains multiple encapsulated triggering agents with varying release times to release one triggering mechanism after another. A second encapsulated triggering mechanism can be used to counteract the first triggering mechanism thereby causing the superabsorbent material to reabsorb. The second encapsulated triggering agent will have a release time greater than the first encapsulated triggering agent. A suitable second release time for the second encapsulated triggering mechanism is about 10 to 120 minutes and at least 5 minutes greater than the first release time. If the first triggering agent includes an acid then the second triggering agent will include a base. If the first triggering agent includes a base then the second triggering agent will include an acid. After the second encapsulated triggering mechanism is released the superabsorbent material will have a third absorbency of suitably at least about 10 grams fluid per gram of superabsorbent material, more suitably at least 15 grams fluid per gram of superabsorbent material, and desirably at least about 20 grams fluid per gram of superabsorbent material.

A third encapsulated triggering mechanism can be used to counteract the second triggering mechanism to cause the superabsorbent material to again deswell. The third encapsulated triggering agent will have a release time greater than the second encapsulated triggering agent. A suitable third release time for the third encapsulated triggering mechanism is about 15 to 180 minutes and at least 5 minutes greater than the second release time. If the second triggering agent includes an acid then the third triggering agent will include a base. If the second triggering agent includes a base then the third triggering agent will include an acid. After the third encapsulated triggering mechanism is released the superabsorbent material has a fourth absorbency of at least about 20% less than the third absorbency, more suitably at least about 25% less than the third absorbency, and desirably at least about 30% less than the third absorbency.

A fourth encapsulated triggering mechanism can be used to counteract the third triggering mechanism to cause the superabsorbent material to again reabsorb. The fourth encapsulated triggering agent will have a release time greater than the third encapsulated triggering agent. A suitable fourth release time for the fourth encapsulated triggering agent is about 20 to 240 minutes and at least 5 minutes greater than the third release time. If the third triggering agent includes an acid then the fourth triggering agent will include a base. If the third triggering agent includes a base then the fourth triggering agent will include an acid. After the fourth encapsulated triggering mechanism is released the superabsorbent material has a fifth absorbency of at least about 10 grams fluid per gram of superabsorbent material, more suitably at least 15 grams fluid per gram of superabsorbent material, and desirably at least about 20 grams fluid per gram of superabsorbent material. It is not applicants' intention to limit the invention to acid/base triggering mechanisms. Acids and bases are used above as triggering mechanism purely for discussion purpose. Other triggering mechanisms can be easily substituted and used in the same fashion by one skilled in the art.

In one embodiment the encapsulated triggering mechanism can be located throughout the absorbent composite. In one embodiment the encapsulated triggering mechanism is located in a predetermined region of the absorbent composite. The predetermined region can be the target area of the absorbent composite. Around the target area can be a second superabsorbent material not affected by the triggering mechanism. The predetermined region of the absorbent composite can also be located outside of the target area or overlapping both the target region and an area outside the target region.

In one embodiment of the invention it has been discovered that conventional superabsorbents can be triggered to deswell by the addition of a solution having a different ion strength. In one embodiment a high ionic strength solution, such as a 20% by weight lithium chloride solution, is added to an absorbent composite with swollen superabsorbent materials. The high ionic strength solution triggers the superabsorbent materials to deswell, releasing the absorbed liquid to the free space of the absorbent composite and surrounding superabsorbent materials. An additional insult of a low ionic strength solution, such as a 0.9% by weight sodium chloride solution triggers the superabsorbent material to reswell and absorb additional liquid. By alternating applications of high and low ionic strength solutions the superabsorbent materials can be triggered to deswell and reswell many times.

Superabsorbent materials capable of swelling and dewelling according to this invention can be distributed throughout the absorbent composite or be localized to predetermined areas of the absorbent composite. FIG. 1 shows absorbent core 25 made of an absorbent composite according to one embodiment of this invention. Absorbent core 25 has a first region 28 having a superabsorbent material capable of swelling and deswelling. First region 28 could also contain the same superabsorbent material as is throughout the absorbent composite and define the area of application of the triggering mechanism. Second region 26 has a superabsorbent material either not deswellable at all or not deswellable by the same triggering mechanism as the superabsorbent material of first region 28. Second region 26 could also contain the same superabsorbent material as first region 28 and be an area which does not include the triggering mechanism. Deswellable superabsorbent materials and triggering mechanisms of the diaper of FIG. 1 can include any embodiments of this invention.

The deswellable superabsorbent material is placed in first region 28 to distribute fluid from the target area to the outer areas of absorbent core 25. In FIG. 1 the target area is first region 28 as it is in the general crotch area of the diaper user, where the body fluids will first contact absorbent core 25. First region 28 is shown in FIG. 1 as a substantially square area where the deswellable superabsorbent material is located. First region 28 can vary in size and shape. In one embodiment first region 28 is in the crotch region of the diaper. In one embodiment first region 28 can be numerous small areas throughout the absorbent composite or a few small areas localized in the crotch region of the diaper. Desirably an area, or areas, containing deswellable superabsorbent materials according to this invention, such as first region 28, covers about 5% to 90% of the surface area of the absorbent composite, more desirably about 10% to 70%, and more desirably between about 20% and 50%.

First region 28 of absorbent core 25 receives the fluid insult from the diaper user. The superabsorbent material in first region 28 swells as the fluid is absorbed. After all, or substantially all, the fluid is retained in absorbent core 25 in and around first region 28, a triggering mechanism is applied to the superabsorbent material in first region 28, resulting in deswelling of the superabsorbent material. The fluid released during deswelling enters the free space of absorbent core 25 and is distributed through capillary forces or other driving forces through the porous absorbent composite to the superabsorbent material located in second regions 26. The superabsorbent material in second regions 26 absorbs the fluid. The result of the deswelling of the superabsorbent material in first region 28 enhances distribution of body fluids away from the target area (first region 28) to the outer areas of the absorbent composite away from the target area. More of absorbent core 25 is utilized as distribution is improved. The superabsorbent in first region 28 can then be reswollen to absorb additional fluid from the free space of the absorbent composite or an additional insult from the user.

Figure 2:
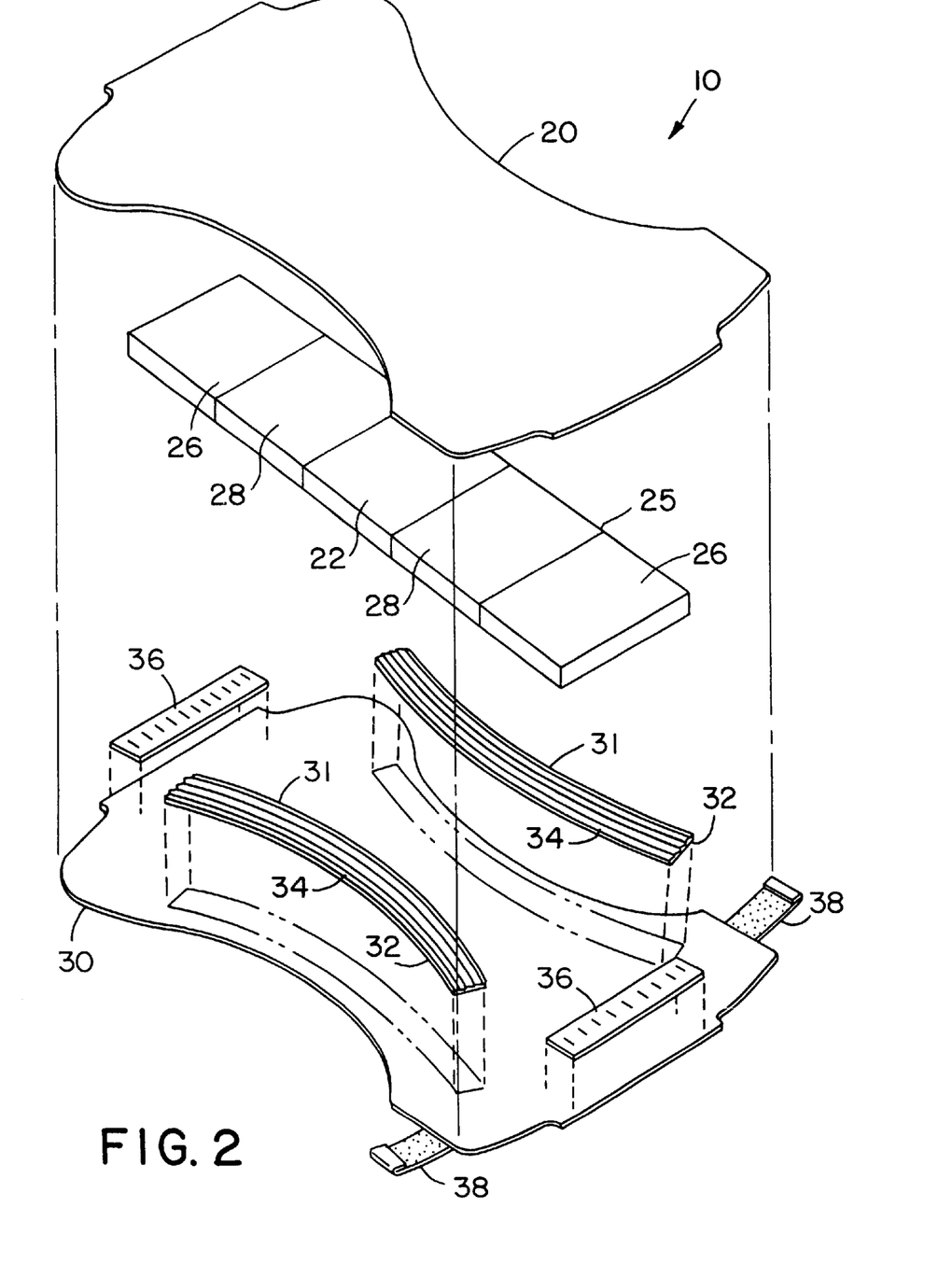
FIG. 2 is an exploded perspective view of an absorbent article according to one embodiment of this invention.

An additional embodiment of an absorbent article of this invention is shown in FIG. 2. In FIG. 2 absorbent composite 25 has a superabsorbent material that swells slowly and is located in target area 22. A superabsorbent material that is capable of swelling and deswelling is placed just outside target area 22 in first regions 28. Normal or fast swelling rate superabsorbent is located in second regions 26 such that the swelling and deswelling superabsorbent is located between the slow swelling rate superabsorbent and the normal or fast swelling rate superabsorbent. The advantage of placing the slow swelling rate superabsorbent in the target area is that this region will maintain capacity for a longer period of time.

Superabsorbent materials useful in this invention can absorb at least about 10 grams of 0.9% by weight sodium chloride solution per gram of superabsorbent, more suitably at least about 15 grams of 0.9% by weight sodium chloride solution per gram of superabsorbent, and desirably 20 grams of 0.9% by weight sodium chloride solution per gram of superabsorbent. The amount of absorption can be determined by weighing the superabsorbent material before adding the liquid (dry weight), and weighing again after adding the liquid (wet weight) and calculating the difference. Deswellable superabsorbents useful in this invention can deswell and release at least about 20% of absorbed liquid within 100 minutes, more suitably at least about 30% of absorbed liquid within 100 minutes, and desirably at least about 40% of absorbed liquid within 100 minutes. The amount of fluid lost during deswelling can also be determined by weighing the superabsorbent material when swollen and by weighing after deswelling and calculating the difference.

In one embodiment of this invention the superabsorbent material can reswell to absorb additional fluid after triggering. Suitably the superabsorbent material can reswell and reabsorb to a level of at least about 10 grams of 0.9% by weight sodium chloride solution per gram of superabsorbent material, more suitably the superabsorbent material can reswell and reabsorb to a level of at least about 15 grams of 0.9% by weight sodium chloride solution per gram of superabsorbent material, and desirably the superabsorbent material can reswell and reabsorb to a level of at least about 20 grams of 0.9% by weight sodium chloride solution per gram of superabsorbent material. Superabsorbent materials of this invention can reswell to a level of at least about 10 grams of 0.9% by weight sodium chloride solution per gram of superabsorbent material in less than 60 minutes, more suitably superabsorbent materials of this invention can reswell to a level of at least about 10 grams of 0.9% by weight sodium chloride solution per gram of superabsorbent material in less than 30 minutes, and desirably superabsorbent materials of this invention can reswell to a level of at least about 10 grams of 0.9% by weight sodium chloride solution per gram of superabsorbent material in less than 15 minutes.

EXAMPLE 1

Swelling/Deswelling by Temperature Sensitive Superabsorbents

N-isopropylacrylamide sodium acrylate (NIPA) copolymer gel was selected to test for temperature sensitive swelling and deswelling. The N-isopropylacrylamide sodium acrylate (NIPA) copolymer gel used in this example was made by Professor Zhibing Hu's Group from University of North Texas, Denton, Tex. The NIPA copolymer gel preparation method can be found in the reference, Z. Hu, X. Zhang, and Y. Li, in Science, Vol. 269, No. 5223, 1995, herein incorporated by reference. The only difference between the samples in this invention and that in the reference is that the NIPA sample in this invention used 10 mM sodium acrylate instead of 8 mM sodium acrylate as in the reference. The temperature sensitivity of the NIPA absorbency was tested at room temperature (about 24° C.) and 54° C., which is above the transition temperature (39° C.) of NIPA gel (54° C. was picked arbitrarily due to the available equipment at the testing site). The test was performed by Centrifuge Retention Capacity (CRC) test.

The CRC can be measured by placing 0.200 grams of the sample material to be tested (the material had a moisture content of less than 5 weight percent) into a water-permeable bag which will contain the sample while allowing the test solution (0.9% by weight sodium chloride solution) to be freely absorbed by the sample. A heat-sealable tea bag material (grade 542, commercially available from Kimberly-Clark Corporation, Neenah, Wis.) works well as a water-permeable bag for most applications. The bag is formed by folding a 5×3 inch sample of the bag material in half and heat sealing two of the open edges to form a 2.5×3 inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. Three sample bags are tested for each superabsorbent material. The sealed bags are placed between two Teflon coated fiberglass screens having ¼ inch openings (Taconic Plastics, Inc., Petersburg, N.Y.) and submerged in a pan of 0.9 percent by weight sodium chloride solution at an assigned temperature (either 24° or 54° C.), making sure that the screens are held down until the bags are completely wetted. After wetting, the samples remain in the solution for an assigned period of time, at which time they are removed from the solution and temporarily laid on a nonabsorbent flat surface. The wet bags are then placed into the basket of a suitable centrifuge capable of subjecting the samples to a g-force of 350. One such suitable centrifuge is a Clay Adams Dynac II, model #0103, having a water collection basket, digital rpm gauge, and machined drainage basket adapted to hold and drain the flat bag samples. The samples must be placed in opposing positions within the centrifuge to balance the basket when spinning. The bags are centrifuged at a target of 1600 rpm for 3 minutes (target g-force of 350). The bags are removed and weighed, with the empty control bags being weighed first, followed by the bags containing superabsorbent material. The amount of fluid absorbed and retained by the superabsorbent material, taking into account the fluid retained by the bag material alone, is the centrifuge retention capacity of the superabsorbent material, expressed as grams of fluid per gram of superabsorbent material.

Each sample was tested at seven conditions summarized in Table 1. After submersing the sample according to the conditions of Table 1 a CRC test was performed on the sample. After the CRC test was completed the sample would be subject to submersion at the next condition, follwed by another CRC test. The results of the test are summarized in Table 1.

TABLE 1

| Condition | Temperature (° C.) | Time at condition (min) | CRC Capacity (g/g) |
|---|---|---|---|
| 1 | 24 | 15 | 14.3 |
| 2 | 54 | 30 | 2.4 |
| 3 | 24 | 30 | 11.8 |
| 4 | 54 | 30 | 2.9 |
| 5 | 24 | 60 | 17.0 |
| 6 | 54 | 30 | 2.9 |
| 7 | 24 | 60 | 16.9 |

As can be seen by the results in Table 1, the NIPA superabsorbent absorbed much more 0.9% by weight sodium chloride solution at room temperature than the amount after deswelling at 54° C.

EXAMPLE 2
Swelling/Deswelling by Ion Strength Changing

Dow superabsorbent XUS 40675.00, a commercially available superabsorbent material manufactured by Dow Chemical, Midland, Mich., was used to demonstrate the swelling and deswelling by changes in ion strength. The superabsorbent was exposed sequentially to 0.9% by weight sodium chloride solution and 20% by weight lithium chloride solution. Specifically, 0.20 grams of superabsorbent material was placed in a teabag. The superabsorbent material was immersed in 75 grams of 0.9% by weight sodium chloride solution for 45 minutes. The saturation amount of the sample was then tested using the centrifuge retention capacity test. The sample was then immersed in 75 grams of 20% by weight lithium chloride solution for 45 minutes. The saturation amount was again tested. These steps were repeated two more times with the 0.9% by weight sodium chloride solution and once more for the 20% by weight lithium chloride solution. Results of the testing are summarized in Table 2.

TABLE 2

| Steps | Amount of solution absorbed (grams solution/gram superabsorbent) |
|---|---|
| First 0.9% by weight sodium chloride solution | 41.6 |
| First 20% by weight lithium chloride solution | 6.8 |
| Second 0.9% by weight sodium chloride solution | 35.5 |
| Second 20% by weight lithium chloride solution | 6.3 |
| Third 0.9% by weight sodium chloride solution | 36.0 |

The results demonstrate the ability to achieve multiple swelling/deswelling cycles by using sequential exposure to solutions having different ionic strengths. Exposure to a high ionic strength solution (20% LiCl by weight) resulted in capacity less than 20% of the initial absorption capacity, and when reexposed to a low ionic strength solution (0.9% NaCl by weight) brought capacity back up to around 85% of initial capacity.

In further demonstration of this discovery, two air-formed absorbent composites were made by a conventional air forming composite line. The following description is meant to be illustrative of an air-forming process used to form the composites of the present invention, but is not meant to be limiting. Several process components may be used to make webs of the present invention. These include first, a method to fiberize pulp sheets into fiberized fluff. These fiberized fluff fibers are conveyed by air into a forming chamber. Second, a method of adding superabsorbent particles is used to meter and convey superabsorbent particles to the forming chamber. The forming chamber causes the fiberized fluff fibers and the superabsorbent particles to become mixed together. A moving forming screen is located at the bottom of the forming chamber. This screen is air permeable and is typically connected to a vacuum source. This vacuum removes air from the forming chamber and causes the fiberized fluff fibers and superabsorbent particles to be deposited onto the forming screen to form a web. Tissue may be unwound onto the forming wire such that the fibers and particles are laid onto the tissue to aid in conveying. The speed of the pulp sheets, superabsorbent feeders, and the forming screen can all be independently adjusted to control the composition and basis weight of the resulting web. Following formation of the web on the forming wire, a roller may be used to compress the web to a desired level. At the end of the forming screen the web is wound into a continuous roll.

Figure 3:
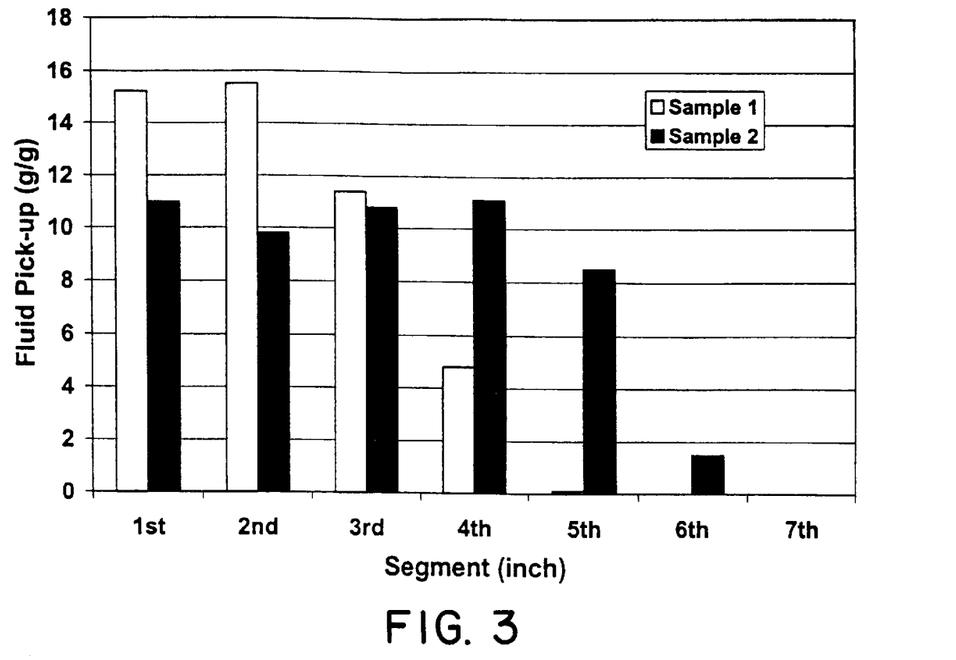
FIG. 3 is a graphical plot of liquid pick-up by an absorbent composite per distance of the absorbent composite, according to one embodiment of this invention.

For this example, each composite contained 40% by weight of Dow XUS 40675.00 superabsorbent and 60% by weight CR-1654 pulp fibers available from Bowater Corporation, Coosa, Ala. Each sample was tested by an inclined wicking test. An example of an inclined wicking test set up is shown in FIG. 7 of European Patent Application EP 0532002A1, herein incorporated by reference. An 11×2 inch wide piece of the two identical composites was placed on an inclined trough that was 30° from the horizontal. Three reservoirs of liquid were prepared on scales, one containing 20% by weight lithium chloride solution and two containing 0.9% by weight sodium chloride solution. An edge of Sample 1 was exposed to only one reservoir containing 0.9% by weight sodium chloride solution. An edge of Sample 2 was exposed first to a reservoir containing 0.9% by weight sodium chloride solution and (after the 20 minute waiting time) subsequently to a second reservoir containing 20% by weight lithium chloride solution. Each sample was exposed to the respective reservoir until about 21 grams of liquid was picked up. A twenty minute wait time occurred between the first and second exposures. The samples were then cut into one-inch segments and weighed to determine the amount of liquid per segment. The fluid pick-up results are summarized in Table 3 and FIG. 3. For the swelling/deswelling composite (Sample 2) the fluid amount in the lower regions of the composite is reduced and the fluid in the upper segments is increased compared to the control composite (Sample 1).

TABLE 3

| | Amount of Solution Absorbed (grams solution/gram of composite) | |
|---|---|---|
| Segment | Sample 1 | Sample 2 |
| First inch | 15.2 | 11.0 |
| Second inch | 15.5 | 9.8 |
| Third inch | 11.4 | 10.8 |
| Fourth inch | 4.8 | 11.1 |
| Fifth inch | 0.1 | 8.5 |
| Sixth inch | 0 | 1.5 |
| Seventh inch | 0 | 0 |

EXAMPLE 3

Swelling/Deswelling by Acid and Base Chemistries

Commercially available superabsorbent material (SAM) Favor 880, manufactured by Stockhausen Inc., Greensboro, N.C., was used to demonstrate using acid and base chemistries to obtain deswell and reswell mechanics. 3.8 grams Favor 880 and 300 grams 0.9% sodium chloride solution were added to a 1000 ml glass beaker. A magnetic stir rod was used to stir the solution for 30 minutes. After stirring, the approximate volume of the swollen superabsorbent gel was recorded. 100 ml of 1.16 weight % hydrochloric acid solution was added into the beaker and the solution was stirred for 10 minutes and the volume was recorded. 100 ml 1.26 weight % sodium hydroxide solution was added to the beaker and stirred for 10 minutes and the volume of the superabsorbent gel was recorded. The addition of the HCl and NaOH solutions was repeated once more for each, the volume of superabsorbent gel recorded each time. When the same volume of the 1.16 weight % hydrochloric acid solution and 1.26 weight % sodium hydroxide solution are used the resulting solution is a 0.9% by weight sodium chloride solution. The results from this experiment are summarized in Table 4.

TABLE 4

| Steps | Addition Step | Stirring time at each step (min) | Approximate Gel Volume (ml) |
|---|---|---|---|
| 1 | 4 g SAM in 300 g 0.9% by weight sodium chloride solution | 30 | 210 |
| 2 | Add 100 ml HCl solution | 10 | 60 |
| 3 | Add 100 ml NaOH solution | 10 | 210 |
| 4 | Add 100 ml HCl solution | 10 | 50 |
| 5 | Add 100 ml NaOH solution | 10 | 200 |

The results in Table 4 show that the addition of an acid solution can be used to deswell a swollen superabsorbent material and that addition of a base solution can be used to reswell an acidified superabsorbent material. The response time of the swelling and deswelling using acid and base chemistry is less than 10 minutes.

Figure 5:
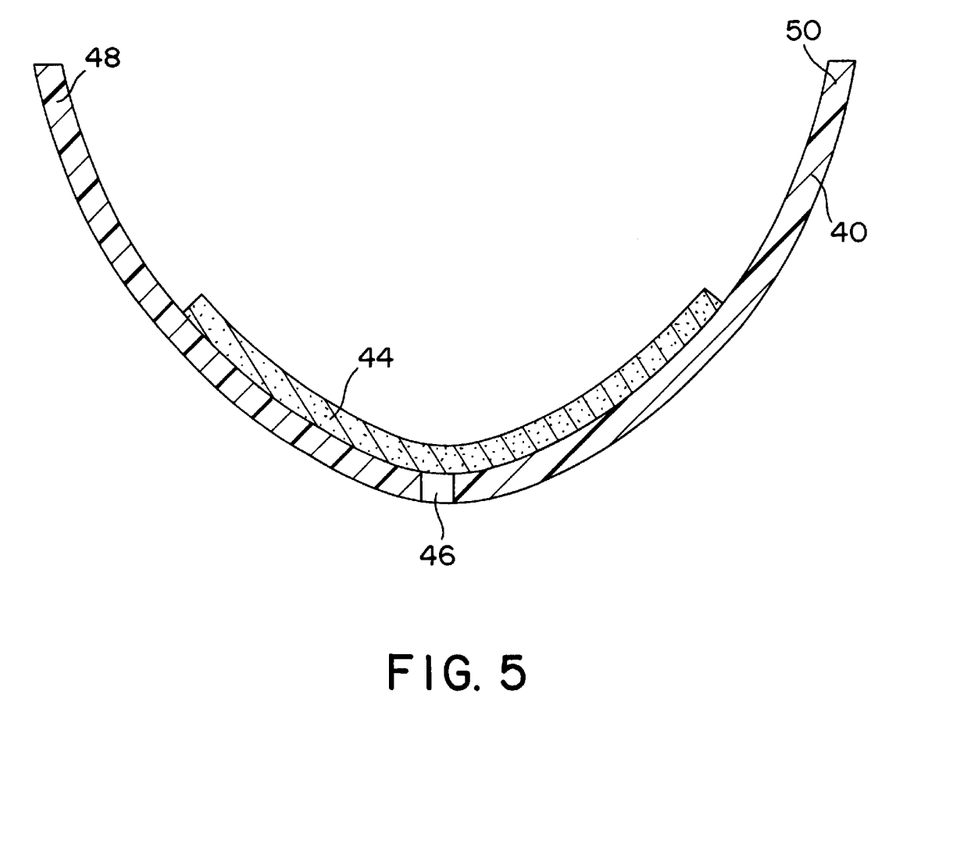
FIG. 5 is a schematic of a cradle testing apparatus used in the test procedure described below.

In order to test the effect of acid-base chemistry on swelling/deswelling superabsorbent material for liquid distribution, a cradle test was performed on an air formed absorbent composite made using the method described in example 2. The cradle test equipment can be referred to as the Multiple Insult Test (MIST Evaluation) as described in U.S. Pat. No. 6,152,904 herein incorporated by reference. FIG. 5 shows a cradle test apparatus and the testing of these examples is briefly described by the following. Referring to FIG. 5, the sample air-formed absorbent composites 44 is weighed, and placed in the valley of an acrylic cradle 40, against the inner wall of the cradle. The cradle has a length (into the page) of 33 cm with front and back ends blocked off, a height of 19 cm, a distance between upper arms 48 and 50 of 30.5 cm, and an angle between the upper arms of 60 degrees. The cradle has slot 46 at its lowest point. A water-impermeable tape was used to seal the slot to prevent liquid run-off during the test.

Two identical air-formed absorbent composites were made having 40% by weight Favor 880 superabsorbent material and 60% by weight CR-1654 wood pulp fibers. The samples, Samples 3 and 4, were 15 inches long by 2 inches wide and had a basis weight of 400 grams per square meter and a dry density of about 0.2 grams per cubic centimeter. Tests were run in which a total of 99 gram of liquid was added per sample by three 33 gram insults.

The first insult to the center of the absorbent composites (at the bottom of cradle 40) added to both samples was 33 grams 0.9% sodium chloride solution. The intervals between each of the three insults for each sample was 30 minutes. For Sample 3, the second insult was 33 grams of 1.16% hydrochloric acid solution to trigger the superabsorbent material to deswell. For Sample 4, the second insult was 33 grams 0.9% by weight sodium chloride solution. For Sample 3, the third insult was 33 grams of 1.26% sodium hydroxide solution to neutralize the hydrochloric acid and trigger the superabsorbent material to reswell. The addition of the 33 grams 1.26% sodium hydroxide solution to the 33 grams 1.16% hydrochloric acid solution resulted in 66 grams of 0.9% by weight sodium chloride solution. For Sample 4, the third insult was 33 grams 0.9% sodium chloride solution. The total resulting solution added to both samples by the completion of the test was 99 grams 0.9% by weight sodium chloride solution.

Based on visual observation during the test the insults of the acid and base triggers remained concentrated to a three to four inch long target area in the mid-section of the composite. Therefore the primary area where the superabsorbent material swelled and deswelled was in or near the target. Visual observation of the wicking distances of liquid up the sides of the cradled composite revealed better distribution of liquid in Sample 3 which was trigger to swell and deswell. The wicking distance was measured at the end of each 30 minute wait time. After the first insult, as expected, the wicking distances were about equal. After the second insult the wicking distance up each side of the cradle was about three centimeters farther for Sample 3 than Sample 4. After the third insult the wicking distance up each side of the cradle for Sample 3 was about two centimeters farther than Sample 4.

Figure 4:
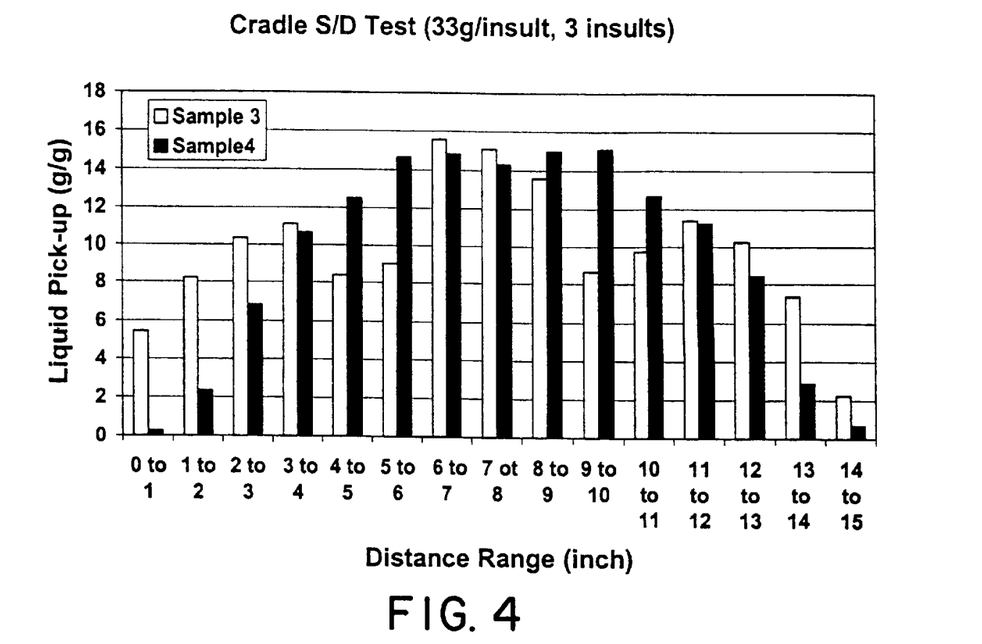
FIG. 4 is a graphical plot of liquid pick-up by an absorbent composite per distance of the absorbent composite, according to one embodiment of this invention.

Samples 3 and 4 were then cut into fifteen one-inch sections and weighed. The weight of each section was compared to the dry weight of the one-inch section, determined by dividing the total dry weight by 15 inches. Table 5 summarizes the fluid pickup results for Samples 3 and 4. FIG. 4 shows a plot of the liquid pick-up, in grams liquid/grams section, of each section of both samples plotted against the distance range of the section in inches. Section 7–8 is the middle of the absorbent composite where the insults were applied.

TABLE 5

| Distance Range (inch) | Amount of Solution Absorbed (grams solution/gram of composite) | |
|---|---|---|
| | Sample 3 | Sample 4 |
| 0–1 | 5.43 | 0.28 |
| 1–2 | 8.20 | 2.36 |
| 2–3 | 10.33 | 6.86 |
| 3–4 | 11.10 | 10.65 |
| 4–5 | 8.39 | 12.50 |
| 5–6 | 9.04 | 14.65 |
| 6–7 | 15.58 | 14.82 |
| 7–8 | 15.08 | 14.30 |
| 8–9 | 13.58 | 14.95 |
| 9–10 | 8.64 | 15.08 |
| 10–11 | 9.75 | 12.66 |
| 11–12 | 11.38 | 11.23 |
| 12–13 | 10.25 | 8.44 |
| 13–14 | 7.36 | 2.89 |
| 14–15 | 2.24 | 0.72 |

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. An absorbent composite, comprising:
  a water-insoluble fibrous matrix;
  a superabsorbent material having a first absorbency of at least about 10 grams 0.9% by weight sodium chloride solution per gram of superabsorbent material; and
  a first encapsulated triggering mechanism having a first release time of between about 5 and 60 minutes;
  wherein the superabsorbent material has a second absorbency of at least about 20% less than the first absorbency after a release of the encapsulated triggering mechanism.

2. The absorbent composite of claim 1, further comprising:
  a second encapsulated triggering mechanism having a second release time of between 10 and 120 minutes and at least about 5 minutes longer than the first release time;
  wherein the superabsorbent material has a third absorbency of at least about 10 grams 0.9% by weight sodium chloride solution per gram of superabsorbent material after a release of the second encapsulated triggering mechanism.

3. The absorbent composite of claim 2, further comprising:
  a third encapsulated triggering mechanism having a third release time of between about 15 and 180 minutes and at least about 5 minutes longer than the second release time;
  wherein the superabsorbent material has an fourth absorbency of at least about 20% less than the third absorbency after a release of the third encapsulated triggering mechanism.

4. The absorbent composite of claim 3, further comprising:
  a fourth encapsulated triggering mechanism having a fourth release time of between 20 and 240 minutes and at least about 5 minutes longer than the third release time;
  wherein the superabsorbent material has a fifth absorbency of at least about 10 grams 0.9% by weight sodium chloride solution per gram of superabsorbent material after a release of the fourth encapsulated triggering mechanism.

5. The absorbent composite of claim 1, wherein the superabsorbent material is an anionic superabsorbent and the first encapsulated triggering mechanism comprises an acid.

6. The absorbent composite of claim 1, wherein the superabsorbent material comprises a cationic superabsorbent and the first encapsulated triggering mechanism comprises a base.

7. The absorbent composite of claim 6, further comprising a second encapsulated triggering mechanism, wherein the second encapsulated triggering mechanism comprises an acid.

8. The absorbent composite of claim 5, further comprising a second encapsulated triggering mechanism, wherein the second encapsulated triggering mechanism comprises a base.

9. The absorbent composite of claim 7, further comprising a third encapsulated triggering mechanism, wherein the third encapsulated triggering mechanism comprises a base.

10. The absorbent composite of claim 8, further comprising a third encapsulated triggering mechanism, wherein the third encapsulated triggering mechanism comprises an acid.

11. The absorbent composite of claim 10, further comprising a fourth encapsulated triggering mechanism, wherein the fourth encapsulated triggering mechanism comprises a base.

12. The absorbent composite of claim 9, further comprising a fourth encapsulated triggering mechanism, wherein the fourth encapsulated triggering mechanism comprises an acid.

13. The absorbent composite of claim 1, wherein the first encapsulated triggering mechanism is located in at least one predetermined region of the absorbent composite.

14. The absorbent composite of claim 13, wherein the first encapsulated triggering mechanism is located in a target area of the absorbent composite.

15. The absorbent composite of claim 13, wherein the first encapsulated triggering mechanism is located outside a target area of the absorbent composite.

16. The absorbent composite of claim 1, wherein the first encapsulated triggering mechanism is located throughout the absorbent composite.

17. The absorbent composite of claim 13, wherein the first encapsulated triggering mechanism is located in more than one predetermined region of the absorbent composite.

18. The absorbent composite of claim 1, wherein the superabsorbent material has a form selected from the group consisting of particles, fibers, filaments, film, and combinations thereof.

19. The absorbent composite of claim 1, wherein the water-insoluble fibrous matrix comprises a material selected from the group consisting of natural fibers, synthetic fibers, and combinations thereof.

20. The absorbent composite of claim 19, wherein the water-insoluble fibrous matrix comprises a material selected from the group consisting of wood pulp fluff, cotton, wool, silk, polyethylene, polypropylene, polyester, nylon, polyvinyl alcohol, polyacrylonitrile, polyvinyl chloride, and combinations thereof.

21. The absorbent composite of claim 1, wherein the superabsorbent material comprises a temperature sensitive polymer.

22. The absorbent composite of claim 21, wherein the superabsorbent material comprises N-isopropylacrylamide-sodium acrylate polymer.

23. The absorbent composite of claim 1, wherein the superabsorbent material can deswell about at least 20% of the absorbed sodium chloride solution within 100 minutes after release of the first encapsulated triggering mechanism.

24. The absorbent composite of claim 1, wherein the superabsorbent material can deswell about at least 20% of the absorbed sodium chloride solution within 50 minutes.

25. The absorbent composite of claim 1, wherein the superabsorbent material can deswell about at least 20% of the absorbed sodium chloride solution within 10 minutes.

26. The absorbent composite of claim 1, further comprising:
a first region comprising the superabsorbent material; and
a second region comprising a second superabsorbent material;
wherein the second superabsorbent material has an absorbency before the release of the first encapsulated triggering mechanism which is substantially the same as the absorbency after the release of the first encapsulated triggering mechanism.

27. An absorbent composition, comprising:
a superabsorbent material having a first absorbency of at least about 10 grams 0.9% by weight sodium chloride solution per gram of superabsorbent material; and
a first encapsulated triggering mechanism having a first release time of between about 5 and 60 minutes;
wherein the superabsorbent material has a second absorbency of at least about 20% less than the first absorbency after a release of the encapsulated triggering mechanism.

28. The absorbent composition of claim 27, further comprising:
a second encapsulated triggering mechanism having a second release time of between 10 and 120 minutes and at least about 5 minutes longer than the first release time;
wherein the superabsorbent material has a third absorbency of at least about 10 grams 0.9% by weight sodium chloride solution per gram of superabsorbent material after a release of the second encapsulated triggering mechanism.

29. The absorbent composition of claim 28, further comprising:
a third encapsulated triggering mechanism having a third release time of between about 15 and 180 minutes and at least about 5 minutes longer than the second release time;
wherein the superabsorbent material has an fourth absorbency of at least about 20% less than the third absorbency after a release of the third encapsulated triggering mechanism.

30. The absorbent composition of claim 29, further comprising:
a fourth encapsulated triggering mechanism having a fourth release time of between 20 and 240 minutes and at least about 5 minutes longer than the third release time;
wherein the superabsorbent material has a fifth absorbency of at least about 10 grams 0.9% by weight sodium chloride solution per gram of superabsorbent material after a release of the fourth encapsulated triggering mechanism.

31. The absorbent composition of claim 27, wherein the superabsorbent material is an anionic superabsorbent and the first encapsulated triggering mechanism comprises an acid.

32. The absorbent composition of claim 27, wherein the superabsorbent material comprises a cationic superabsorbent and the first encapsulated triggering mechanism comprises a base.

33. The absorbent composition of claim 32, further comprising a second encapsulated triggering mechanism, wherein the second encapsulated triggering mechanism comprises an acid.

34. The absorbent composition of claim 31, further comprising a second encapsulated triggering mechanism, wherein the second encapsulated triggering mechanism comprises a base.

35. The absorbent composition of claim 33, further comprising a third encapsulated triggering mechanism, wherein the third encapsulated triggering mechanism comprises a base.

36. The absorbent composition of claim 34, further comprising a third encapsulated triggering mechanism, wherein the third encapsulated triggering mechanism comprises an acid.

37. The absorbent composition of claim 36, further comprising a fourth encapsulated triggering mechanism, wherein the fourth encapsulated triggering mechanism comprises a base.

38. The absorbent composition of claim 35, further comprising a fourth encapsulated triggering mechanism, wherein the fourth encapsulated triggering mechanism comprises an acid.

39. The absorbent composition of claim 27, wherein the superabsorbent has a form selected from the group consisting of particles, fibers, filaments, film, and combinations thereof.

40. The absorbent composition of claim 27, wherein the superabsorbent material comprises a temperature sensitive polymer.

41. The absorbent composition of claim 40, wherein the superabsorbent material comprises N-isopropylacrylamide-sodium acrylate polymer.

42. The absorbent composition of claim 27, further comprising:
the superabsorbent material; and
a second superabsorbent material;

wherein the second superabsorbent material has an absorbency before the release of the first encapsulated triggering mechanism which is substantially the same as the absorbency after the release of the first encapsulated triggering mechanism.

43. An absorbent article, comprising:
a liquid-permeable body-side liner;
an absorbent composite comprising a superabsorbent material and a first encapsulated triggering mechanism having a first release time of between about 5 and 60 minutes; and
a substantially liquid-impermeable outer cover adjacent the absorbent composite material;
wherein the superabsorbent material is capable of having a first absorbency of at least about 10 grams 0.9% by weight sodium chloride solution per gram of superabsorbent material and is capable of deswelling at least about 20% of the absorbed sodium chloride solution when the first encapsulated triggering mechanism is released to the superabsorbent material, and the superabsorbent material has a second absorbency of at least about 20% less than the first absorbency after a release of the first encapsulated triggering mechanism.

44. The absorbent article of claim 43, wherein the absorbent article comprises a swimpant.

45. The absorbent article of claim 43, wherein the absorbent article comprises a training pant.

46. The absorbent article of claim 43, wherein the absorbent article comprises a feminine care product.

47. The absorbent article of claim 43, wherein the absorbent article comprises a medical absorbent product.

48. The absorbent article of claim 43, wherein the superabsorbent material is capable of absorbing at least about 15 grams 0.9% by weight sodium chloride solution per gram of superabsorbent material and deswelling at least about 20% of the absorbed sodium chloride solution when the first encapsulated triggering mechanism is released to the superabsorbent material.

49. The absorbent article of claim 43, wherein the superabsorbent material is capable of absorbing at least about 20 grams 0.9% by weight sodium chloride solution per gram of superabsorbent material and deswelling at least about 20% of the absorbed sodium chloride solution when the first encapsulated triggering mechanism is released to the superabsorbent material.

50. The absorbent article of claim 43, further comprising:
a second encapsulated triggering mechanism in the absorbent composite;
wherein the superabsorbent material is capable of reabsorbing 0.9% by weight sodium chloride solution to a level of at least about 10 grams 0.9% by weight sodium chloride solution per gram superabsorbent material upon release of the second encapsulated triggering mechanism.

51. The absorbent article of claim 48, wherein the superabsorbent material is capable of reabsorbing an amount of 0.9% by weight sodium chloride solution equal to at least about 15 grams 0.9% by weight sodium chloride solution per gram superabsorbent material upon release of the second encapsulated triggering mechanism.

52. The absorbent article of claim 49, wherein the superabsorbent material is capable of reabsorbing an amount of 0.9% by weight sodium chloride solution equal to at least about 20 grams 0.9% by weight sodium chloride solution per gram superabsorbent material upon release of the second encapsulated triggering mechanism.

53. The absorbent article of claim 43, wherein the superabsorbent material is capable of multiple swelling and deswelling cycles.

54. The absorbent article of claim 43, wherein the first encapsulated triggering mechanism is located throughout substantially all of the absorbent core.

55. The absorbent article of claim 43, wherein the first encapsulated triggering mechanism is located in a predetermined region of the absorbent core.

56. The absorbent article of claim 55, wherein the first encapsulated triggering mechanism is located in a target area of the absorbent composite.

57. The absorbent article of claim 55, wherein the first encapsulated triggering mechanism is located outside a target area of the absorbent composite.

58. The absorbent article of claim 55, wherein the first encapsulated triggering mechanism is located in more than one predetermined region of the absorbent composite.

59. The absorbent article of claim 43, wherein the superabsorbent material comprises a material selected from the group consisting of particles, fibers, filaments, film, gel, and combinations thereof.

60. The absorbent article of claim 43, wherein the absorbent composite further comprises a water-insoluble fibrous matrix comprising a material selected from the group consisting of natural fibers, synthetic fibers, and combinations thereof.

61. The absorbent article of claim 60, wherein the water-insoluble fibrous matrix comprises a material selected from the group consisting of wood pulp fluff, cotton, wool, silk, polyethylene, polypropylene, polyester, nylon, polyvinyl alcohol, polyacrylonitrile, polyvinyl chloride, and combinations thereof.

62. The absorbent article of claim 43, wherein the superabsorbent material comprises an anionic superabsorbent material and the first encapsulated triggering mechanism comprises an acid.

63. The absorbent article of claim 43, wherein the superabsorbent material comprises a cationic superabsorbent material and the first encapsulated triggering mechanism comprises a base.

64. The absorbent article of claim 62, further comprising a second encapsulated triggering mechanism, wherein the second encapsulated triggering mechanism comprises a base.

65. The absorbent article of claim 63, further comprising a second encapsulated triggering mechanism, wherein the second encapsulated triggering mechanism comprises an acid.

66. The absorbent article of claim 43, wherein the superabsorbent material comprises a temperature sensitive polymer.

67. The absorbent article of claim 66, wherein the superabsorbent material comprises N-isopropylacrylamide-sodium acrylate polymer.

68. The absorbent article of claim 43, further comprising:
the superabsorbent material located in at least one first region of the absorbent core; and
a second superabsorbent material located in at least one second area of the absorbent core;
wherein the second superabsorbent material retains absorbency after release of the first encapsulated triggering mechanism.

69. The absorbent article of claim 43, wherein the superabsorbent material can deswell at least about 20% of the absorbed sodium chloride solution within 100 minutes after release of the first encapsulated triggering mechanism.

70. The absorbent article of claim 43, wherein the superabsorbent material can deswell at least about 20% of the absorbed sodium chloride solution within 50 minutes.

71. The absorbent article of claim 43, wherein the superabsorbent material can deswell at least about 20% of the absorbed sodium chloride solution within 10 minutes.

72. The absorbent article of claim 43, wherein the absorbent article comprises a diaper.

73. The absorbent article of claim 43, wherein the absorbent article comprises an adult incontinence garment.

74. The absorbent article of claim 43, further comprising:
a second encapsulated triggering mechanism having a second release time of between 10 and 120 minutes and at least about 5 minutes longer than the first release time;
wherein the superabsorbent material has a third absorbency of at least about 10 grams 0.9% by weight sodium chloride solution per gram of superabsorbent material after a release of the second encapsulated triggering mechanism.

75. The absorbent article of claim 74, further comprising:
a third encapsulated triggering mechanism having a third release time of between about 15 and 180 minutes and at least about 5 minutes longer than the second release time;
wherein the superabsorbent material has an fourth absorbency of at least about 20% less than the third absorbency after a release of the third encapsulated triggering mechanism.

76. The absorbent article of claim 75, further comprising:
a fourth encapsulated triggering mechanism having a fourth release time of between 20 and 240 minutes and at least about 5 minutes longer than the third release time;
wherein the superabsorbent material has a fifth absorbency of at least about 10 grams 0.9% by weight sodium chloride solution per gram of superabsorbent material after a release of the fourth encapsulated triggering mechanism.

77. A method of improving liquid distribution in an absorbent composite having at least one superabsorbent material, the steps comprising:
absorbing liquid into at least some of the superabsorbent material of the absorbent composite;
applying a first triggering mechanism to at least some of the superabsorbent material that deswells at least some of the liquid absorbed in the superabsorbent; and
applying a second triggering mechanism to at least some of the deswelled superabsorbent material, the second triggering mechanism causing the deswelled superabsorbent material to resume absorbency.

78. The method of claim 77, further comprising:
reapplying the first triggering mechanism to the at least some of the superabsorbent material which deswells at least some of the liquid absorbed in the superabsorbent; and
reapplying the second triggering mechanism to at least some of the deswelled superabsorbent material, the reapplying of the second triggering mechanism causing the deswelled superabsorbent material to resume absorbency.

79. The method of claim 77, wherein the superabsorbent material comprises a temperature sensitive superabsorbent material.

80. The method of claim 79, wherein the first triggering mechanism comprises an exothermic substance.

81. The method of claim 79, wherein the first triggering mechanism comprises an endothermic substance.

82. The method of claim 81, wherein the second triggering mechanism comprises an exothermic substance.

83. The method of claim 80, wherein the second triggering mechanism comprises an endothermic substance.

84. The method of claim 77, wherein the first triggering mechanism comprises an acid and the second triggering mechanism comprises a base.

85. The method of claim 77, wherein the first triggering mechanism comprises a base and the second triggering mechanism comprises an acid.

86. The method of claim 77, wherein the first triggering mechanism comprises a salt that increases ionic strength of the liquid.

87. The method of claim 77, wherein the second triggering mechanism comprises a substance capable of reducing the ionic strength of the liquid.

* * * * *